US006211344B1

(12) United States Patent
Kraus et al.

(10) Patent No.: US 6,211,344 B1
(45) Date of Patent: *Apr. 3, 2001

(54) PROCESS FOR PREPARING FACTOR V-DEFICIENT PLASMA, AND A DEFICIENT PLASMA WHICH IS OBTAINED IN THIS WAY

(75) Inventors: Michael Kraus, Marburg; Erika Aillaud, Rauschenberg; Heinz-Hermann Drescher, Neustadt, all of (DE)

(73) Assignee: Dade Behring Marburg GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/915,585

(22) Filed: Aug. 21, 1997

(30) Foreign Application Priority Data

Aug. 24, 1996 (DE) ................................. 196 34 312

(51) Int. Cl.⁷ .................... A61K 35/16; C07K 14/745
(52) U.S. Cl. .................... 530/413; 530/380; 530/381; 530/383; 530/384; 424/530
(58) Field of Search ............... 424/530; 530/380, 530/381, 383, 384, 413

(56) References Cited

U.S. PATENT DOCUMENTS

| | | |
|---|---|---|
| 4,139,415 | * 2/1979 | Yin et al. . |
| 5,021,243 | * 6/1991 | Becker et al. . |
| 5,049,491 | * 9/1991 | Mann et al. . |
| 5,705,395 | * 1/1998 | Griffin et al. . |

FOREIGN PATENT DOCUMENTS

| | | |
|---|---|---|
| 0281 089 A2 | 9/1988 | (EP) . |
| 0711 838 A1 | 5/1996 | (EP) . |
| WO 95/01571 | 1/1995 | (WO) . |
| WO 96/15457 | 5/1996 | (WO) . |

OTHER PUBLICATIONS

Axén, Rolf et al., "Chemical Coupling of Peptides and Proteins to Polysaccharides by Means of Cyanogen Halides," *Nature*, vol. 214, pp. 1302–1304 (1967).
Janssen, Catherine L. et al., "Conditions For Stabilization and Determination of Activated Factor V," *Thrombosis Research*, vol. 5, pp. 315–325 (1974).
Kraus, Michael et al., "Coagulation Assay With Improved Specificity to Factor V Mutants Insensitive to Activated Protein C," *Thrombosis Research*, vol. 80, pp. 255–264 (1995).
Stormorken, H., "The Preparation of Proaccelerin Deficient (Parahemophilia) Plasma for the Assay of Proaccelerin," *Scandinav. J. Clin. & Lab. Investigation*, pp. 273–276 (1957).
Williams et al. *Hematology* Fourth Edition, McGraw Hill Publishing Co. New York 1972.*
Kapiotis et al. Am. J. Clin. Pathol. 106:588, Nov. 1996.*
Katzman et al. PNAS 78:162, 1981.*
Cowan et al Am J. Clin Pathol. 1971.*
Sheppard Dissertation Abstracts International vol. 50/10–B, p. 4370, 1988.*

* cited by examiner

*Primary Examiner*—David Saunders
*Assistant Examiner*—Amy De Cloux
(74) *Attorney, Agent, or Firm*—Finnegan, Henderson, Farabow, Garrett & Dunner, L.L.P.

(57) ABSTRACT

The invention relates to a process for preparing factor V-deficient plasma, in particular a factor V-deficient plasma from a starting plasma using antibodies, and a deficient plasma which is obtained in this way.

18 Claims, No Drawings

PROCESS FOR PREPARING FACTOR V-DEFICIENT PLASMA, AND A DEFICIENT PLASMA WHICH IS OBTAINED IN THIS WAY

The invention relates to a process for preparing deficient plasmas, in particular a factor V-deficient plasma, from a starting plasma using antibodies.

A factor V-deficient plasma is understood as being a plasma which is suitable for blood coagulation investigations and is free of factor V but which contains, at essentially normal concentration, all the other coagulation factors which are normally present in the plasma.

A factor V-deficient plasma is suitable, in combination with suitable coagulation tests, for determining the content of activatable or inactivatable factor V in factor V-containing fluids, for example blood or plasma.

The principle of such a determination consists in maxing the sample to be determined with an excess of factor V-deficient plasma and carrying out a coagulation test of known type. The result of this coagulation test then depends only on the content of factor V which is present in the blood sample or plasma sample under investigation, since all the remaining coagulation factors are present in excess and consequently not rate-limiting for the reaction.

In order to determine activatable factor V, a thromboplastin time (TPT), for example, is determined for the sample mixture. In this case, a coagulation activator, i.e. thromboplastin in the case of the TPT, phospholipids and calcium chloride are added to the patient sample which has been mixed with the deficient plasma and the coagulation time is determined. In the absence of factor V, the coagulation of the mixture is slowed down markedly, while in the presence of factor V the coagulation time is shortened in dependence on the factor V activity which is present. This method has been described, for example, by H. Stormorken (The preparation of proaccelerin deficient (parahemophilia) plasma for the assay of proaccelerin. Scand J Clin Lab Invest 9: 273, 1957).

In order to determine inactivatable factor V, an activated partial thromboplastin time (APTT), for example, is carried out on the sample mixture in the presence of activated protein C (see, for example: Kraus, M., Zander, N. and Fickenscher, K.: Coagulation assay with Improved specificity to factor V mutants insensitive to activated protein C. Thrombosis Research, 80: 255–264, 1995; and EP 0 711 838). In the presence of a normally inactivatable factor V, the coagulation time in the presence of activated protein C is prolonged as compared with the APTT. However, if factor V cannot be inactivated by activated protein C, the prolongation is then less pronounced.

The sensitivity of the determination of activatable factor V, in particular, depends crucially on the quality of the deficient plasma employed with regard to the residual content of factor V in the deficient plasma, since the determination is carried out using an excess of deficient plasma and, as a consequence, even a small proportion of factor V, for example 1% residual activity, can no longer be tolerated.

When inactivatable factor V is determined, discrete values are to be expected because this determination is carried out for the purpose of detecting a genetic defect which is also termed factor V disorder. Thus, in a heterozygous carrier of inactivatable factor V, the prolongation of the coagulation time is approx. 50%, while in a homozygous carrier it is close to 0%. On the other hand, the determination of activatable factor V is directed, in particular, to the detection of acquired deficiencies which appear, for example, during operations or in association with liver damage, so that values for activatable factor V can be expected within the entire concentration range. The detection of very low concentration of activatable factor V, for example within a range of between 1 and 10%, is particularly important for diagnosis. The risk of patients with a factor V deficiency suffering uncontrolled internal bleeding increases very markedly below 10% factor V activity. A particularly exact determination is therefore required in this range in order to decide on a therapy, for example using fresh plasma. If the residual activity of the factor V is in the range from about 1 to 5% in a deficient plasma which is supplied in excess, the coagulation test becomes insensitive, i.e. the reference curve becomes too flat, with the result that reliable measurements cannot be carried out in the critical, low concentration range between about 1 and 10%.

A useful deficient plasma should therefore have a factor V activity which is markedly less than 1% of the normal activity.

A deficient plasma of the quality which the above account indicates is imperative can be the plasma of patients who themselves have factor V activities which are markedly less than 1%. A deficient plasma of this type is naturally rare and is not available in sufficient quantity for routine purposes, and ethical problems are attached to obtaining blood donations from patients who are suffering from this severe form of hemophilia.

It is therefore necessary to look for other ways of preparing a suitable deficient plasma. In this context, the possibility suggests itself of destroying the factor V by physicochemical means, with, for example, factor V being denatured, and thereby inactivated, by adding EDTA (ethylenedinitrilotetraacetic acid) and heating. The method of Janssen et al. (Janssen, C. L., Wijngaards, G. and van der Meer, J.: Conditions for stabilization and determination of activated factor V. Thrombosis Research 5: 315–325, 1974) represents an example of this approach. However, this deficient plasma is not suitable for determining inactivatable factor V since factor VIII is also destroyed by adding EDTA (see EP 0 711 838).

Another known method consists in removing factors immuno-adsorptively by means of antibodies. Specific antibodies are bound to an insoluble support material, and the plasma is brought into contact with this support material, to which the specific antibody is bound, so that the relevant factor is removed from the plasma, thereby making it possible to prepare a deficient plasma. In contrast with the above-described chemical methods, other factors, in particular factor VIII, which is important for determining inactivatable factor V, are not destroyed. For this reason, it is only deficient plasmas which have been prepared in this way which can be used for determining inactivatable and activatable factor V (see EP 0 711 838; Kraus et al. 1995).

However, factor V-deficient plasmas which have hitherto been prepared by the immunoadsorptive method are markedly inferior to the chemical method in their sensitivity with regard to activatable factor V. This is demonstrated by way of example in Example 1, in which reference curves for determining activatable factor were constructed using chemically prepared and immunoadsorptively prepared factor V-deficient plasmas, respectively. In the case of the plasma which was purified immunoadsorptively in accordance with the state of the art, the spread of the reference curve in the critical region between factor V contents of 1% and 10% is only about 40% of the spread which was obtained using the chemically prepared plasma.

The use of a combination of antibodies against two different antigens has also been described already, for example in EP 0 281 089 for the purpose of preparing a factor VIII-deficient plasma. Since factor VIII:C is bound to von Willebrand factor in the plasma, an appropriately high quality, i.e. low concentrations of factor VIII:C, was only achieved using a combination of an immunoadsorptive purification against von Willebrand factor and then an immunoadsorptive purification against factor VIII:C. However, in this method, the sequence of the purification steps is important as is the fact that the antibodies employed are of high specificity. By contrast, the sequence of the purification steps is of no significance in the process according to the invention and antibodies are used twice against the same antigen.

The invention was therefore based on the object of developing a process for preparing a factor V-deficient plasma, which process exhibits high sensitivity, which is comparable to that of previous chemical methods, in the determination of activatable factor V and also permits the determination of inactivatable factor V.

The immunoadsorptive methods of the state of the art for preparing deficient plasmas use either polyclonal antibodies or monoclonal antibodies. It has now been found, surprisingly, that when a combination of polyclonal antibodies and monoclonal antibodies is used, a factor V-deficient plasma can be prepared at a quality which is at least comparable with, and in the present case even superior to, that which is achieved using the chemical method. It was not possible to achieve this quality either with a combination of several monoclonal antibodies or with polyclonal antibodies alone; surprisingly, it was only possible to achieve this quality with a combination of the two adsorption steps, with the sequence of these steps being unimportant.

Expediently, the process is carried out by binding the polyclonal or monoclonal antibodies against factor V to insoluble support materials and then bringing these materials into contact with the starting plasma to be treated.

In this connection, the polyclonal and monoclonal antibodies can either be employed in separate fractions or else in a mixture. The immunoadsorption can take place in accordance with methods which are known per se for this purpose, that is, for example, either batchwise or in columns, with it being possible in this case, too, either to use separate columns for each antibody type or to introduce a mixture of the two antibody types into one column.

The insoluble support materials are preferably materials which are available commercially and which are known per se to the skilled person.

The antibodies which are used are, on the one hand, polyclonal and, on the other hand, monoclonal antibodies against human factor V, which antibodies are supplied commercially by a variety of manufacturers.

In the process according to the invention, other factors can be supplied subsequently, by means of adding factor concentrates, after factor V has been removed immunoadsorptively. For this purpose, commercially available preparations are used which are free of factor V in order to ensure that the quality of the deficient plasma is not subsequently reduced once again.

Preferably, the deficient plasma is topped up with purified factor VIII or a factor VIII/von Willebrand factor mixture and/or factor IX to concentrations of from 0.5 to 2, particularly preferably of from 0.8 to 1.2, U/ml.

Known neutralizers, such as protamine sulfate or hexadimethrine bromide (trade name: Polybrene), can also be added at concentrations of from 1 to 20 mg/l, particularly preferably at concentrations of from 3 to 10 mg/l, for the purpose of neutralizing heparin.

The process which has been described makes it possible to prepare a factor V-deficient plasma which contains less then 1% of the normal value of factor V and which gives a sensitivity in the determination of activatable factor V which is comparable to that achieved with chemically prepared factor V-deficient plasmas while at the same time also making it possible to determine inactivatable factor V.

Preferably, the spread of the reference curve in the critical region of a factor V content of from 1 to 10% is at least 50%, very much more preferably at least 70%, of the spread in the case of a chemically prepared, i.e. chemically inactivated, deficient plasma; particularly preferably, the spread is at least 90% of, or is superior to, that which is achieved in the case of a chemically prepared, i.e. chemically inactivated, deficient plasma.

The process which has been described can also be used to prepare plasmas which are deficient in other factors in order to achieve an increased sensitivity in the range of from 1 to 10% of the sought-after factor in coagulation tests. In this context, deficient plasmas can also be produced which are deficient in relation to more than one factor.

The invention is clarified by means of the following examples. Unless otherwise indicated, the reagents of Behringwerke AG, Marburg, Germany, were used.

COMPARATIVE EXAMPLE

Comparison of the sensitivities, with regard to the determination of activatable factor V, of factor V-deficient plasmas which have been prepared chemically and immunoadsorptively in accordance with the state of the art.

Making use of a plasma having a calibrated factor V content (standard human plasma, prod. no. ORKL; FV content: 100%), reference curves were constructed using the following factor V-deficient plasmas: chemically prepared factor V-deficient plasma (factor V-deficient plasma, prod. no. ORSM) and immunoadsorptively prepared factor V-deficient plasma (factor V-deficient plasma, prod. no. 291020, from Baxter, Unterschleissheim, Germany), respectively. For this, the standard plasma was first of all diluted down to concentrations of 100, 50, 10 and 1% with imidazole buffer solution (prod. no. OQAA) and then further diluted 1:20 with imidazole buffer solution once again. Imidazole buffer solution itself was used as the 0% value. 100 μl of the relevant factor V-deficient plasma and 100 μl of the sample dilution were mixed in a coagulometer (from Amelung, Lemgo, Germany) and the mixture was heated at +37° C. for 60 seconds. Coagulation was triggered by adding 200 μl of a thromboplastin reagent (Thromborel S, prod. no. OUHP), which had been previously brought to a temperature of +37° C., and the coagulation time was determined.

The coagulation times which were obtained with the respective commercially available factor V-deficient plasmas are listed in Table 1. It can be seen that the total spread, and in particular the sensitivity in the region below a factor V content of 10%, which region is so important for determining activatable factor V, are about 60% less for the immunoadsorptively prepared factor V-deficient plasma as compared with those for the chemically prepared factor V-deficient plasma.

Table 1:

Coagulation times in seconds which were obtained when calibrating the determination of activatable factor V using 2 commercial factor V-deficient plasmas which were prepared using previous methods.

In addition, the difference in the coagulation times between factor concentrations of 10 and 1%, respectively, is recorded as a measure of the sensitivity in detecting factor V.

| Factor V concentration [%] | Chemically prepared FV-deficient plasma | Immuno-adsorptively prepared FV-deficient plasma |
|---|---|---|
| 0 | 109.3 | 59.0 |
| 1 | 102.5 | 57.0 |
| 10 | 72.5 | 45.0 |
| 50 | 46.8 | 32.2 |
| 100 | 38.1 | 26.0 |
| 10%–1% difference | 30.0 | 12.0 |

EXAMPLE 1

Immunoadsorptive Preparation of Factor V-Deficient Plasma

In order to prepare factor V-deficient plasma in accordance with the invention, 10 mg of the relevant antibodies were in each case covalently immobilized on 5 g of cyanogen bromide-activated Sepharose (from Pharmacia, Uppsala, Sweden). The coupling reaction followed a published method (Axen, R. et al., Nature, 214: 1302, 1967) in accordance with the manufacturer's instructions. A total of 7 different monoclonal antibodies were investigated. The antibodies listed in Table 2 (obtained from Behringwerke AG) were selected for the investigations which are described in the examples. There were no quantitative differences as compared with the results reported in the examples.

Subsequently, the immunoadsorbent was in each case washed with phosphate-buffered sodium chloride solution (PBS; 0.15 mol/l, pH 7.2) and acetic acid (0.5 mol/l, pH 2.5). Prior to use, each adsorbent was packed into its own column and equilibrated with 3 times the gel volume of PBS. Citrate plasma from human blood was passed through one column or a chain of consecutive columns and the eluate was collected in fractions. For the subsequent analyses, only those fractions were used which had been maximally adsorbed in order to exclude any falsification of the results arising from possible differences in the adsorptive capacity of the column. For this purpose, the factor V content was determined in each fraction. Only those fractions were used which had the longest coagulation time in the factor V determination and a factor V content which was markedly less than 1%. Furthermore, only those fractions were used which did not differ in their behaviour from the first fractions after achieving optimum quality in the respective run. According to these criteria, the capacity of a combination of 750 mg of Mab 95-240/05 and 360 mg of Pab, for example, was 6000 ml of human plasma. However, only about 2 ml were required for the investigations in the following examples.

Table 2:
Antibodies used in the examples.

| Designation | Type |
|---|---|
| Pab | Rabbit polyclonal antibodies |
| 95-240/05 | Monoclonal antibody |
| 95-275/033 | Monoclonal antibody |

EXAMPLE 2

Comparison of the sensitivities, with regard to the determination of activatable factor V, of factor V-deficient plasmas which have been prepared using different immiunoadsorptive methods.

The immunoadsorbents which were prepared in Example 1 were used, either alone or in different combinations, for preparing factor V-deficient plasma. The analysis of the sensitivity for detecting activatable factor V was carried out as described in Example 1.

The coagulation times which were obtained with these different combinations are listed in Table 3. The difference between the coagulation times at 10 and 1% factor V content is recorded under "Sens.", as a measure of the sensitivity, while the total spread of the reference curve between 0 and 100% is recorded in the "Total" line. It can be seen that it was not possible to produce a quality of a factor V-deficient plasma which corresponds to the chemically produced product in Example 1, Table 1, using either polyclonal antibodies alone or using monoclonal antibodies alone or in combinations of several monoclonal antibodies. It was only the combination of the polyclonal antibody and a monoclonal antibody which yielded a quality which was not only comparable but even about 10% superior with regard to sensitivity, while at the same time giving approximately the same total spread of the reference curve. In this context the sequence of the adsorption steps is unimportant.

Table 3:
Coagulation times in seconds when calibrating the determination of activatable factor V employing factor V-deficient plasmas which were prepared using different combinations of immunoadsorbents.

"Sens." =difference in the coagulation times at factor V concentrations of 10 and 1%, respectively, as a measure of detection sensitivity; "Total" =total spread of the reference curve between 100 and 0% factor V contents. Factor V conc. =factor V concentration. A1 and A2 =1st and 2nd, respectively, antibodies used for the immunoadsorption. For the designation of the antibodies which were used on the adsorbents, see Tab. 2.

| Factor V conc. [%] | A1 A2 | 95-240/05 — | Pab — | 95-240/05 95-275/033 | Pab 95-240/05 | 95-240/05 Pab |
|---|---|---|---|---|---|---|
| 0 | | 43.1 | 78.6 | 45.8 | 96.9 | 94.6 |
| 1 | | 43.0 | 71.8 | 43.8 | 83.0 | 86.0 |
| 10 | | 37.0 | 48.3 | 37.5 | 50.0 | 50.0 |
| 50 | | 28.2 | 31.0 | 28.0 | 31.5 | 32.5 |
| 100 | | 24.0 | 25.8 | 23.7 | 25.5 | 26.4 |
| Sens. | | 6.0 | 23.5 | 6.3 | 33.0 | 36.0 |
| Total | | 19.1 | 52.8 | 22.1 | 71.4 | 68.2 |

EXAMPLE 3

Suitability of the factor V-deficient plasma which has been prepared in accordance with the invention for determining inactivatable factor V (factor V disorder)

A factor V-deficient plasma which had been prepared using the combination according to the invention of a polyclonal and a monoclonal immunoadsorption was tested for its suitability for detecting an inactivatable factor V. For this, the coagulation times of a normal plasma pool (standard human plasma; prod. no. ORKL, from Behringwerke AG) and a citrate plasma from a donor suffering from a heterozygous factor V disorder defect were determined on a coagulometer (Behring Coagulation Timer, from Behringwerke AG) using ProcC APC (prod. no. OQKF, from Behringwerke AG). For carrying out the determination, 10 µl of plasma sample were mixed with 40 µl of factor V-deficient plasma, and 50 µl of a contact phase activator (Pathromtin SL; prod. no. OQGS) were added. For determining the APTT, the coagulation was started, after incubating at +37° C. for 2 min, by adding 50 µl of 25 mmol/l calcium chloride solution; for determining the APTT in the presence of activated protein C (APCT), the coagulation was triggered, after incubating at +37° C. for 3 min, by adding the APC reagent (contains activated protein C and calcium chloride) which is included in the kit. The coagulation times were determined and are recorded in Table 4.

When the factor V-deficient plasma which was prepared in accordance with the invention is used, a prolongation of the APTT by 57.5 sec is found for a pool of normal blood donors in the test for factor V disorder, with this prolongation being due to inactivation of the normal factor V by the presence of activated protein C. In the case of a heterozygous factor V-disorder carrier, on the other hand, half of the factor V molecules present in the plasma are altered such that they are only very slowly inactivated by activated protein C, whereas the procoagulatory activity remains unaffected by this. Accordingly, only approximately ½ the prolongation of the coagulation time, as compared with the normal plasma pool, is therefore to be expected under the influence of activated protein C, which is what is correspondingly obtained with a prolongation of only 27.5 sec.

The process according to the invention is consequently suitable for providing a factor V-deficient plasma which is of adequate quality for determining the inactivatability of factor V as well.

Table 4:

Testing the suitability of the factor V-deficient plasma which is prepared in the process according to the invention for detecting a factor V-disorder defect. APTT=activated partial thromboplastin time; APCT=APTT in the presence of activated protein C. Coagulation time values are in seconds.

| Coagulation test | Factor V-disorder defect | Normal plasma pool |
|---|---|---|
| APTT | 50.5 | 48.3 |
| APCT | 78.0 | 105.8 |
| APCT - APTT difference | 27.5 | 57.5 |

What is claimed is:

1. A process for preparing a factor V-deficient plasma capable of detecting inactivatable factor V from a starting plasma using antibodies against factor V, which comprises purifying the starting plasma by immunoadsorption with monoclonal and polyclonal antibodies against factor V.

2. The process as claimed in claim 1, wherein the starting plasma is treated with polyclonal antibodies in a first step and with monoclonal antibodies in a second step.

3. The process as claimed in claim 1, wherein the starting plasma is treated with monoclonal antibodies in a first step and with polyclonal antibodies in a second step.

4. The process as claimed in claim 1, wherein the starting plasma is treated with a mixture of polyclonal antibodies and monoclonal antibodies.

5. The process as claimed in claim 1, wherein the said antibodies are bound to insoluble, commercially available support materials.

6. The process as claimed in claim 1, wherein antibodies against human factor V which were isolated from any homeothermic species, are used as the polyclonal antibodies.

7. The process as claimed in claim 1, wherein antibodies against human factor V are used as the monoclonal antibodies, with one or more different clones being employed.

8. The process as claimed in claim 1, wherein factor VIII:C, von Willebrand factor or a von Willebrand factor/factor VIII:C mixture is added to the factor V-deficient plasma before or after the preparation in order to achieve concentrations of 0.6–2 U/ml in the factor V-deficient plasma.

9. The process as claimed in claim 1, wherein factor IX is added to the factor V-deficient plasma before or after the preparation in order to achieve factor IX concentrations of 0.6–2 U/ml in the factor V-deficient plasma.

10. The process as claimed in claim 9, wherein factor VIII:C, von Willebrand factor or a von Willebrand factor/factor VIII:C mixture is added.

11. The process as claimed in claim 1, wherein heparin neutralizers are added at concentrations of from 1 to 20 mg/l.

12. A factor V-deficient plasma which is prepared as claimed in claim 1.

13. The process as claimed in claim 6, wherein the homeothermic species is rabbit, sheep, chicken or goat.

14. The process as claimed in claim 7, wherein only antibodies of one clone are employed.

15. The process as claimed in claim 8, wherein the concentrations in the factor V-deficient plasma are 0.8–1.2 U/ml.

16. The process as claimed in claim 9, wherein the concentrations in the factor V-deficient plasma are 0.8–1.2 U/ml.

17. The process as claimed in claim 11, wherein the heparin neutralizers are protamine sulfate or hexadimethrine bromide.

18. The process as claimed in claim 11, wherein the concentration of the heparin neutralizers is from 3 to 10 mg/l.

* * * * *